(12) United States Patent
Syska et al.

(10) Patent No.: US 8,220,079 B2
(45) Date of Patent: Jul. 17, 2012

(54) PORTACATH PROTECTION DEVICE

(75) Inventors: Robert W. Syska, Sayville, NY (US); Cathleen A. Syska, Sayville, NY (US)

(73) Assignee: Port Guard USA, Inc., Sayville, NY (US)

( * ) Notice: Subject to any disclaimer, the term of this patent is extended or adjusted under 35 U.S.C. 154(b) by 343 days.

(21) Appl. No.: 12/510,646

(22) Filed: Jul. 28, 2009

(65) Prior Publication Data

US 2011/0023218 A1 Feb. 3, 2011

(51) Int. Cl.
*A41D 13/00* (2006.01)
(52) U.S. Cl. .......................................................... 2/463
(58) Field of Classification Search .............. 2/455, 463, 2/464, 69, 94; 128/888, 889, 95.1, 113.1
See application file for complete search history.

(56) References Cited

U.S. PATENT DOCUMENTS

| | | | |
|---|---|---|---|
| 4,272,847 A | 6/1981 | Buhler | |
| 4,317,237 A | 3/1982 | Porte et al. | |
| 4,373,211 A | 2/1983 | Goudreau et al. | |
| 4,397,636 A | 8/1983 | Ganshaw | |
| 5,106,331 A | 4/1992 | Lizarazu | |
| 5,245,706 A | 9/1993 | Moschetti et al. | |
| 5,337,417 A | 8/1994 | Whiteside et al. | |
| 5,621,914 A * | 4/1997 | Ramone et al. | 2/463 |
| 5,950,249 A | 9/1999 | Clement | |
| 6,320,093 B1* | 11/2001 | Augustine et al. | 602/41 |
| 6,576,808 B1* | 6/2003 | Dreyer | 602/42 |
| 7,100,216 B2 | 9/2006 | Matechen et al. | |
| 7,152,246 B2 | 12/2006 | Infante | |
| 7,237,270 B2 | 7/2007 | Crye et al. | |
| 7,503,080 B2* | 3/2009 | Link | 2/463 |
| 7,765,615 B2* | 8/2010 | Eastwood et al. | 2/115 |
| 7,877,820 B2* | 2/2011 | Landi et al. | 2/463 |
| 2005/0256621 A1* | 11/2005 | Lange | 701/45 |
| 2006/0080762 A1* | 4/2006 | Kobren et al. | 2/463 |
| 2008/0178371 A1 | 7/2008 | Landi et al. | |
| 2008/0202531 A1* | 8/2008 | Fletcher | 128/888 |
| 2008/0235855 A1* | 10/2008 | Kobren et al. | 2/463 |
| 2009/0126087 A1* | 5/2009 | Armstrong et al. | 2/455 |
| 2010/0024100 A1* | 2/2010 | Sokolowski et al. | 2/455 |
| 2010/0024101 A1* | 2/2010 | Berner et al. | 2/455 |

* cited by examiner

*Primary Examiner* — Khoa Huynh
*Assistant Examiner* — Amber Anderson
(74) *Attorney, Agent, or Firm* — Schiff Hardin LLP

(57) ABSTRACT

A device and system for protecting a surgically implanted medical port from damage during daily physical activities consisting of a protective shield that may be placed at any location on a port protection shirt.

7 Claims, 4 Drawing Sheets

PORTACATH PROTECTION DEVICE

FIELD OF THE INVENTION

The present invention relates to a protective device for covering a surgically implanted port. More specifically, the protective device is configured to protect a surgically implanted port from damage or injury during daily physical activities and is capable of being placed over different areas on the upper chest or arms of a user depending on the placement of the port.

BACKGROUND OF THE INVENTION

Persons undergoing intensive medical treatment may be required to have repeated injections of drugs or multiple drawing of blood samples. To ease patient discomfort associated with repeated needle sticks, the patient may elect to have a port or portacath (a portmanteau of "portal" and "catheter") surgically implanted beneath the skin. Various types of portacaths are available and go by various names, such Port-a-Cath, Microport, Bardport, PowerPort (power injectable), Passport, Infuse-a-Port, Medi-Port, and Lifesite (for hemodialysis patients). Another commonly used term is totally implantable venous access system (TIVAS). Additionally, portacaths are a form of a "central venous access device" and are frequently referred to as such in the medical field.

The port has a septum through which drugs can be injected and blood samples can be drawn many times. The port consists of a reservoir compartment (the portal) that has a silicone bubble (the septum) for needle insertion and a catheter or an attached plastic tube. The device is surgically inserted under the skin in the upper chest or in the arm, and appears as a bump under the skin. It requires no special maintenance and is completely internal, so swimming and bathing are not a problem. The catheter runs from the portal and is surgically inserted into a vein, usually the jugular vein, subclavian vein, or superior vena cava. Ideally, the catheter terminates in the superior vena cava, just upstream of the right atrium. This position allows infused agents to be spread throughout the body quickly and efficiently.

The septum is made out of a special self-sealing silicone rubber and can be punctured hundreds of times before it weakens significantly. To administer treatment or to withdraw blood, the port is located and the area is disinfected. The port is then accessed by puncturing the overlaying skin with a needle. When the port is no longer needed, the port can be removed through a surgical operation.

Ports have many different uses, such as total parenteral nutrition, delivery of chemotherapy, delivery of coagulation factors, the withdrawing of blood from patients requiring frequent blood tests, delivery of antibiotics, and the delivery of various medications.

Since the port is surgically implanted under the skin, there is a risk that the persons having such a port may damage it during the course of daily physical activities, especially for sports activities and the like. During such physical activities, people who have a port sometimes experience pain when physical contact is made with their port. Persons with a port are at a risk of rupturing the structural sutures that hold the port in place. It is also possible that the catheter may be ruptured or torn loose.

In the past, the only option for persons with a port was to have a specially made device for the protection of the port. As an example, pediatric chest guards are designed for children who have had surgery in the thoracic region or who have a port placed in their upper chest wall. The first step in making the pediatric chest guard involves taking individual measurements and creating a pattern. Splinting materials are molded to the patient's chest and back so that the end product contours to the patient's body and allows the upper extremities freedom of movement. An anterior chest piece and a posterior back piece are held in place using riveted straps made from stockinette and velcro strips. The chest guard allows children to safely return to their normal daily activities such as participation in gym classes, playing with friends, or engaging in extracurricular sports. Another option is to modify pads and belts designed for other sports, such as football, and sew a pocket onto a shirt at the location of the port. Usually the shirt would be slightly smaller than normal so that it fits snugly and does not shift. The pad is then inserted into the pocket to protect the port location.

Also available as a form of protection is a series of products for protecting the heart from impact during sports. These so-called "heart guards" protect persons from getting hurt by getting hit in the chest, for example, with a baseball, which could adversely effect the heart. Heart guards are intended to be located in the center of the wearer's chest and thus lack the ability to protect a port from damage since the port may be located in any of a number of different areas and varies depending on the patient.

For these reasons, it would be advantageous to have a protective device for a port that is shaped and sized to protect the port location from injury and is capable of being located at any position along the chest or upper arms of a user.

BRIEF DESCRIPTION OF THE DRAWINGS

The foregoing and other features of the present invention will be more readily apparent from the following detailed description and drawings of the illustrative embodiments of the invention in which.

DETAILED DESCRIPTION

Figure 1:
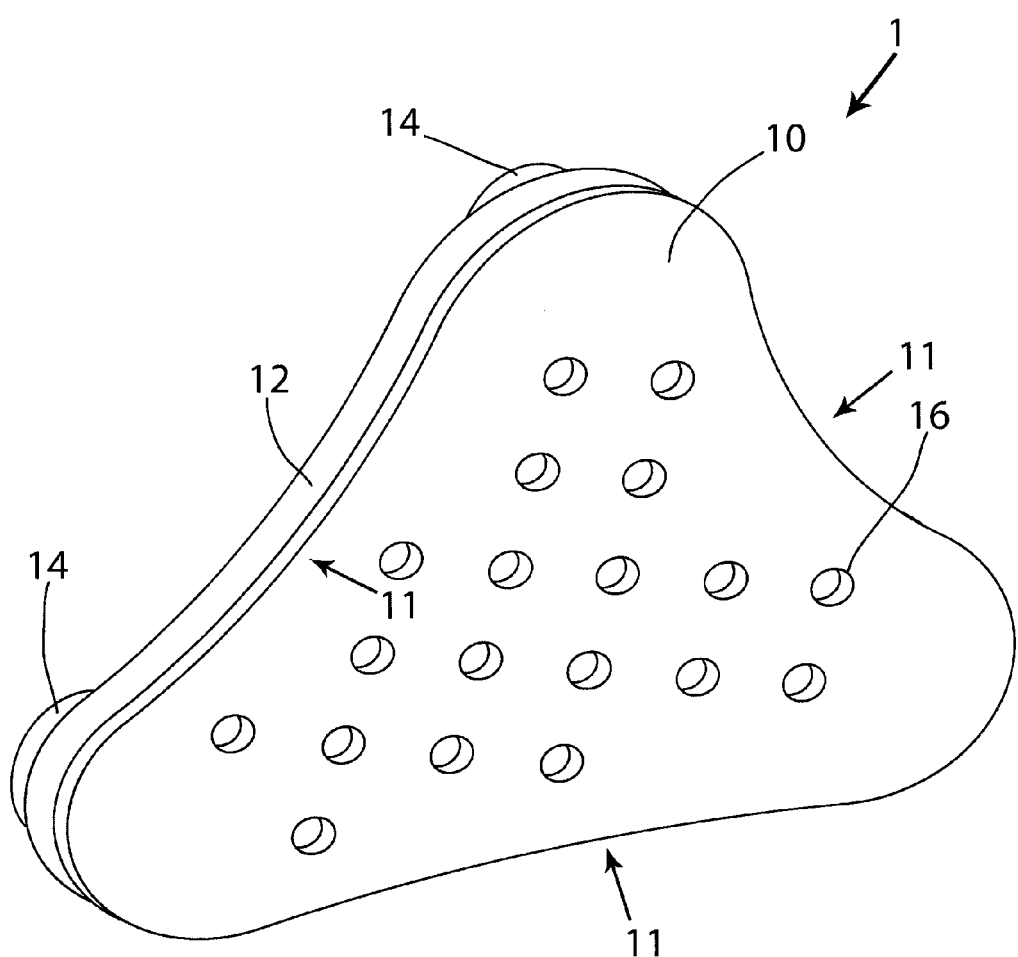
FIG. 1 is a front perspective view of one embodiment of the invention.

Various embodiments of the present invention will be described in detail with reference to the drawings, where like reference numerals represent like parts and assemblies throughout the several views. Reference to various embodiments does not limit the scope of the invention, which is limited only by the scope of the claims attached hereto. Additionally, any examples set forth in this specification are not intended to be limiting and merely set forth some of the many possible embodiments for the claimed invention.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

Figure 2:
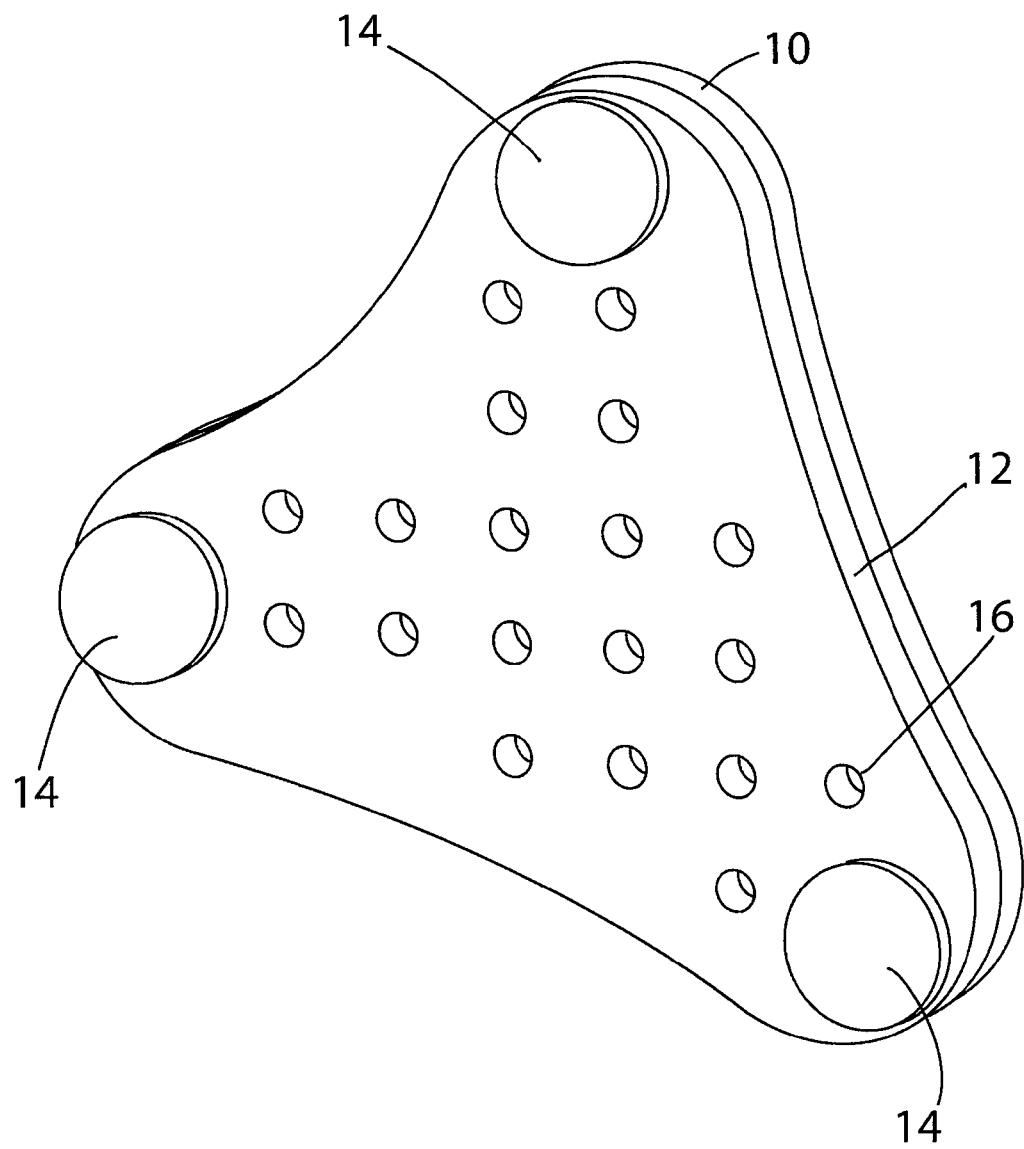
FIG. 2 is a bottom perspective view of one embodiment of the present invention.
Figure 3:
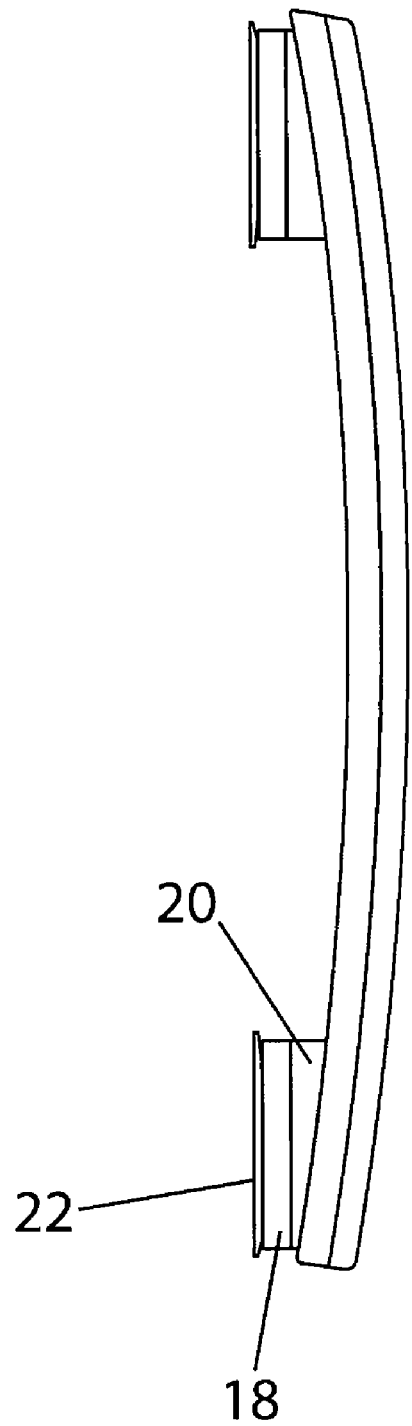
FIG. 3 is a side view of one embodiment of the present invention.

Port protector device 1 is shown in FIGS. 1 through 3. Port 1 may be comprised of protective shield 10, absorption layer 12 and supports 14. Protective shield 10 may be formed of plastic, aluminum, polymer or any other material or combination of materials capable of resisting impact that may occur against the chest or arm of a user. Preferably, protective shield 10 will be capable of slight deflection on impact so as to diminish the force of the impact. In one embodiment of the invention, on the underside of protective shield 10 is an absorption layer 12. Absorption layer 12 may be made of a foam or any similar material that can compress and absorb an impact against protective shield 10. In another embodiment of the invention, absorption layer 12 would only occur at the locations of supports 14. Supports 14 may be located at three locations along the periphery of the device. Supports 14 space protective shield 10 from the body of the user and may be made of plastic, rubber or the like. On the lower side of supports 14 is located an attachment device, such as velcro hooks. Alternatively, protective shield 10 may be shaped so as to have three contact points at which velcro hooks may be attached without using separate supports.

Protective shield 10 is dimensioned with a length and width so as to extend beyond the periphery of an implanted port. Since most implanted ports are generally circular in nature, the device may have substantially the same length and width. Protective shield 10 may also be concave so that the center height of the device is greater than the height at the peripheral edges, as shown in FIG. 3. In one embodiment, protective shield 10 may have cutaway portions 11 which give the protective shield a shape resembling a symmetrical "Y". The term "symmetrical extensions" means each of the arms of the "y" shape, which are relatively equal in size and shape. The symmetrical extensions have a bottom surface defining a plane with the center of the shield extending above the plane. Supports 14 may be attached or coupled to the bottom surface of each symmetrical extension. Supports 14 will extend below the plane, so as to space the center of the device further from the port of the user when port protection device 1 is in use. The reason for removing the material as shown at cutaway portions 11 is that the device will be held above the user's body by only those three points so as to provide a snug fit for the patient. In addition, any impact on the device will cause energy to be dissipated at the location of the three supports. By removing the extra material along the edges as shown at positions 11, the comfort of the user is increased because there is potentially less surface area of the device contacting the wearer and there is less chance that those edges will cause irritation when contacting the body of the wearer.

Protective shield 10 may be in other forms, dimensions or shapes that provide suitable protection for an implanted port. Protective shield 10 may also contain holes 16 that pass entirely through the device. Holes 16 increase ventilation and therefore improve the comfort of the user, especially during sporting activities. In yet another embodiment as shown in FIG. 3, supports 14 may be comprised of foam section 18, a compressible material 20 and velcro hooks 22. Compressible material 20 may have the same functionality as absorption layer 12.

Figure 4:
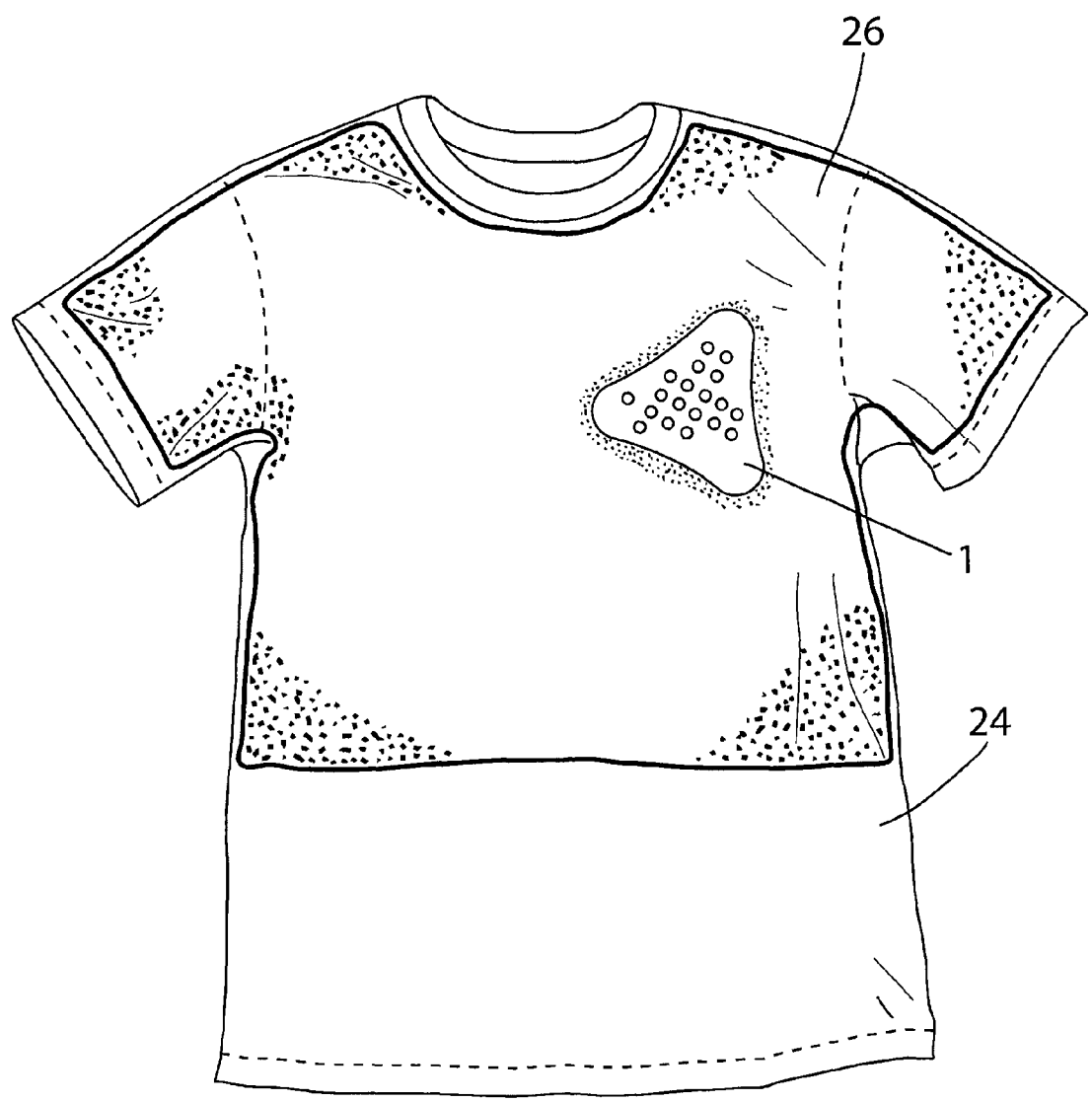
FIG. 4 is a front view of the protection device used in combination with a port protection shirt of the present invention.

FIG. 4 shows the placement of port protector device 1 on protection shirt 24. Protection shirt 24 is generally an undergarment or shirt, such as what is commonly known as a compression shirt. It is intended to be a relatively tight fitting shirt that the user may wear, either alone or underneath other clothing. Protection shirt 24 will have port attachment material 26 located on its external surface along the upper thoracic region and upper arm locations where a port may be located. Material 26 may be a device such as the velcro loops that interact with the velcro hooks of protective device 1 to maintain protective device 1 in place. Other attachment devices may be used to ensure that protective device 1 may be removably attached in any location on the shirt that corresponds to a location of a portacath of a user.

In use, the user will wear the shirt and then simply place protective device 1 over the implanted port. The device is held in place by the velcro hooks on the bottom of supports 14 attaching to the velcro loops on the outside of protection shirt 24. On impact against protective shield 10, energy may be dissipated through the flexing of protective shield 10, absorption of energy through absorption layer 12 and/or dissipation of the impact energy through supports 14 onto the body of the user.

While the invention has been particularly shown and described with reference to preferred embodiments thereof, it would be understood by those skilled in the art that various changes in form and details may be made therein without departing from the spirit and scope of the invention.

What is claimed as new and desired to be protected is:

1. A device for protecting an implantable port comprising:
   a concave protective shield having three substantially peripheral bottom surface locations that define a plane with a radial center of the shield extending a distance above the plane;
   three supports located at the three substantially peripheral bottom surface locations, with the three supports each extending a second distance below the plane with each support having a bottom surface;
   a plurality of hooks covering substantially all of the bottom surface of the three supports; and
   a protection shirt having a plurality of loops on an anterior external surface in substantially all of a thoracic region of the shirt, whereby the hooks on the bottom surface of the three supports are capable of interacting with the loops on the protection shirt to hold the concave protective shield in place over the implantable port in multiple different locations within the anterior thoracic region of the shirt where the loops are located.

2. The device of claim 1 further comprising:
   an absorption layer attached to the protective shield.

3. The device of claim 1 wherein the protective shield contains two or more holes for providing ventilation.

4. A system for protecting an area of an anterior thorax region of a person comprising:
   a concave protective shield having three symmetrical extensions with bottom surfaces of the extensions defining a plane and a radial center of the shield extending a distance above the plane;
   a peripheral bottom surface of the protective shield between the symmetrical extensions at least partially extending above the plane but below the distance above the plane;
   three supports coupled to the bottom surfaces of the extensions on one end of the supports and a touch fastener covering the other end of the supports; and
   a protection shirt having a mating touch fastener on an anterior external surface in substantially all of a thoracic region of the shirt, whereby the touch fastener on the supports is capable of interacting with the mating touch fastener on the protection shirt to hold the concave protective shield in place in multiple different locations within the anterior thoracic region of the shirt where the mating touch fastener is located.

5. The system of claim 4 further comprising:
an absorption layer attached to the protective shield.

6. The system of claim 4 wherein the protective shield contains two or more holes for providing ventilation.

7. A system for protecting an implantable port comprising:
a concave protective shield having three substantially peripheral bottom surface locations that define a plane with a radial center of the shield extending a distance above the plane; the protective shield having radial symmetry wherein the radius of the protective shield from the radial center to the outside edge increases and then decreases at locations 120 degrees apart, which locations 120 degrees apart correspond to the three substantially peripheral bottom surface locations;

a port protection shirt having a touch fastener on an anterior external surface of the shirt that permits placement of the protective shield at multiple different locations in the thoracic region where the touch fastener is located; and a detachable connector having a mating touch fastener between the three substantially peripheral bottom surface locations and the port protection shirt, wherein the protective shield may be detachably placed on the port protection shirt at multiple different locations corresponding to a location of a surgically implanted port within the thoracic region.

* * * * *